United States Patent [19]

Wu et al.

[11] 4,153,635

[45] May 8, 1979

[54] PREPARATION OF CUMENE HYDROPEROXIDE

[75] Inventors: Ching-Yong Wu, O'Hara Township, Allegheny County; Harold E. Swift, Gibsonia; John E. Bozik, Plum Borough, all of Pa.

[73] Assignee: Gulf Research & Development Company, Pittsburgh, Pa.

[21] Appl. No.: 859,291

[22] Filed: Dec. 12, 1977

Related U.S. Application Data

[63] Continuation-in-part of Ser. No. 748,729, Dec. 9, 1976, abandoned.

[51] Int. Cl.² ............................................ C07C 179/04
[52] U.S. Cl. ..................................................... 568/574

[58] Field of Search ..................................... 260/610 B

[56] References Cited

U.S. PATENT DOCUMENTS

| 2,632,774 | 3/1953 | Conner | 260/610 B |
| 3,187,055 | 6/1965 | Armstrong et al. | 260/610 B |

FOREIGN PATENT DOCUMENTS

676772  8/1955  United Kingdom ................ 260/610 B

*Primary Examiner*—Werren B. Lone

[57] ABSTRACT

Cumene hydroperoxide is prepared by the oxidation of cumene with molecular oxygen in the presence of a minute amount of solid barium oxide.

10 Claims, No Drawings

PREPARATION OF CUMENE HYDROPEROXIDE

This application is a continuation-in-part of our application Ser. No. 748,729, filed Dec. 9, 1976, now abandoned.

FIELD OF THE INVENTION

This invention relates to cumene hydroperoxide and more particularly it relates to the preparation of cumene hydroperoxide by the oxidation of cumene using molecular oxygen in the presence of a catalyst.

DESCRIPTION OF THE PRIOR ART

U.S. Pat. No. 2,632,774 describes the preparation of cumene hydroperoxide from cumene by oxidation of the cumene with molecular oxygen using one percent and two percent calcium hydroxide as a catalyst. Other alkali metal and alkaline earth metal compounds, including barium oxide, are listed as catalysts with the amount used being dependent on the specific compound used as the catalyst.

SUMMARY OF THE INVENTION

We have discovered a barium oxide catalyzed process for preparing cumene hydroperoxide by the oxidation of cumene with molecular oxygen at substantially maximum reaction rate and selectivity to cumene hydroperoxide. More particularly, we have discovered that these benefits result when cumene is oxidized in the presence of a minute amount of barium oxide. Additionally we have discovered that the presence of a large amount of barium oxide, although it increases the rate of cumene oxidation as well as the yield of cumene hydroperoxide over that resulting with no barium oxide present, produces larger quantities of undesirable by-products and surprisingly lowers the rate of cumene oxidation over that resulting with a minute amount of barium oxide.

Certain hydrocarbons can be oxidized to the hydroperoxide by direct oxidation using molecular oxygen. In particular, hydrocarbons having a hydrogen atom on a tertiary carbon atom are relatively easy to oxidize to a hydroperoxide in good yield. Other hydrocarbons are more difficult to oxidize to the hydroperoxide and the resulting hydroperoxide is itself quite unstable. Cumene which contains both a tertiary carbon atom and an aromatic ring is comparatively easy to oxidize and can be directly to concentrations as high as 50 percent and higher. Furthermore, according to Lloyd in *Methods in Free Radical Chemistry*, Vol. 4, edited by Huyser (1973), cumene hydroperoxide decomposes at a temperature above 80° C. As a result of this relative stability, cumene hydroperoxide is the only aromatic hydroperoxide which has been commercially available.

A significant problem associated with the oxidation of cumene to form cumene hydroperoxide is the production of undesirable by-products, including alpha-methylstyrene, acetophenone, and alpha, alpha-dimethylbenzyl alcohol. The presence of alpha-methylstyrene in the cumene hydroperoxide is especially undesirable when the cumene hydroperoxide is used to produce phenol and acetone by decomposition of the cumene hydroperoxide with acid. In this decomposition reaction the alpha-methylstyrene will form various tar-like oligomers which end up as difficult to remove impurities in the product phenol.

In U.S. Pat. No. 2,632,774 barium oxide has been included in a list of basic substances stated to be catalysts for the oxidation of cumene to cumene hydroperoxide. We have, in fact, ascertained that the presence of barium oxide in the reactor does increase the yield of cumene hydroperoxide, but we have also surprisingly discovered that the presence of barium oxide steadily decreases the selectivity of the reaction to cumene hydroperoxide as the amount of barium oxide is increased from a maximum selectivity with a minute amount of barium oxide. We believe that this reduction in the selectivity to cumene hydroperoxide results from the concurrent decomposition of the cumene hydroperoxide catalyzed by the excess barium oxide. But, in addition, we have surprisingly discovered that both optimum reaction rate to cumene hydroperoxide as well as substantially maximum selectivity occurs in the presence of a minute amount of barium oxide.

When cumene is oxidized to cumene hydroperoxide, the primary aromatic by-products alpha-methylstyrene, alpha, alpha-dimethylbenzyl alcohol and acetophenone represent a process loss. Generally, the fuel value of these organic by-products represents their true value in the process. Therefore, in carrying out the oxidation reaction of cumene, it is most desirable to reduce the losses, if possible, while increasing the speed of this relatively slow reaction to cumene hydroperoxide. By our invention we have unexpectedly discovered that maximum rate of reaction and substantially maximum selectivity to cumene hydroperoxide can be concurrently induced when a minute amount of barium oxide, that is a minimum amount of about 0.005 weight percent and a maximum amount of about 0.15 weight percent, is present during the oxidation reaction. It is highly unexpected that barium oxide is a superior catalyst for the desired reaction in these minute amounts. Furthermore, this is unexpected because it is contrary to general experience to find selectivity and reaction rate in a chemical reaction concurrently reaching a maximum at the same reaction conditions.

In our procedure for preparing cumene hydroperoxide with barium oxide catalyst, the barium oxide is preferably introduced into the reactor as a finely divided powder in order to accelerate its dispersion throughout the liquid and hasten its availability as a catalyst. Therefore, it is preferred that the initial particle size be small enough to stay in suspension in the liquid phase. However, larger sized particles of barium oxide even including pellet size can be used since the stirring or agitation of the reactor contents will gradually break down and disperse the barium oxide, including this larger sized barium oxide, throughout the solution. Therefore, the initial particle size of the barium oxide can broadly range from about 20 microns to about 5 millimeters in diameter and preferably a particle size ranging between about 50 and about 1,000 microns is used.

When the solution containing the powdered barium oxide is heated up under agitation, a fairly rapid, distinct change in appearance occurs at about 90° C. This change can be described as a transition from a powdery appearance to a milky appearance. This transition to a milky solution is concomitant with the oxidation reaction, indicative of some type of interaction, probably physical, between the barium oxide and the organic phase to form a more initimate association. We believe that this transition is related to the unexpected catalytic effect exhibited by barium oxide. The experimental data suggests to use that a minute amount of the barium oxide is involved in this transition and that it is this barium oxide that is responsible for the positive catalytic effect and the concomitant increased selectivity. The experimental data further suggests that the excess of barium oxide above this minute amount is not involved in this transition but remains in solid particulate form and that it is this solid barium oxide that is responsible for the lowered selectivity.

This transition to a milky solution upon heating this organic solution containing dispersed barium oxide and these catalytic effects are believed to be unique with barium oxide since they are not observed with conventional bases, such as solid sodium hydroxide which does not exhibit a significant catalytic effect. When the stirring of this milky solution is stopped while the elevated temperature is maintained, the solution retains its milky appearance. When the unstirred solution is cooled to room temperature, it reverts to its powdery appearance and the barium oxide precipitates out, resulting in a clear solution. The oxidation reaction is carried out under anhydrous conditions since the presence of water results in lowered selectivity as well as a reduced rate of oxidation.

In order to obtain beneficial results in accordance with our invention, a minute amount of barium oxide is used for the oxidation of cumene to cumene hydroperoxide. Significant improvement in yield and selectivety to cumene hydroperoxide results when barium oxide is used in an amount as low as about 0.0005 weight percent based on the cumene, but we prefer that at least about 0.001 percent barium oxide be used for a more significant improvement and we most prefer that at least about 0.002 be used. The maximum amount of barium oxide to obtain the desired catalytic effect of this invention should not exceed about 0.15 weight percent although higher amounts can be used, if desired, at reduced selectivity and yield. We prefer that the maximum amount of barium oxide does not exceed about 0.12 weight percent and most prefer that it not exceed about 0.1.

In the oxidation of cumene to cumene hydroperoxide, both the reaction rate and the product stability are a function of temperature. The temperature of the reactant cumene solution can be as low as about 90° C., but we prefer that it be at least about 95° C. for a suitable rate of reaction. The maximum temperature should not exceed about 130° C. because of the greatly increasing instability of the product cumene hydroperoxide at the higher temperatures. We prefer that the reaction temperature not exceed about 120° C.

The oxidation of the cumene by our procedure can conveniently be carried out in a batch reaction in which the molecular oxygen is bubbled through the cumene solution at an appropriate elevated temperature and pressure. A suitable elevated pressure is required, sufficient to maintain the cumene in solution at the temperature of reaction. Any suitable source of molecular oxygen, such as air or pure oxygen, can be used. When the oxygen is mixed with diluent gas, it is important that the diluent be free of any reactive contaminant gas, such as a nitrogen oxide or an oxide of sulfur, which would adversely react with one or more of the components in the reaction vessel. The partial pressure of oxygen in the reaction vessel is not critical. We prefer that the partial pressure of oxygen in the reaction zone be at least about 10 psia (68.9 kPa) but a partial pressure of oxygen as low as about 5 psia (34.5 kPa) is useful. The partial pressure of oxygen can be as high as about 200 psia (1,376 kPa) or even higher, but we prefer that the partial pressure be no greater than about 30 psia (207 kPa).

It is desirable that a minor amount of a hydrocarbon hydroperoxide be initially present in the cumene to eliminate the substantial induction time required to initiate the oxidation reaction and therefore to substantially increase the rate of oxidation in the early phase of the oxidation reaction. This hydroperoxide is desirably used in an amount up to about 5 weight percent based on the cumene used. Higher amounts can be present but do not exert an additional beneficial effect. It is preferred to use at least about 0.5 eight percent of the initiator hydroperoxide. Most preferably the hydroperoxide initiator is the same hydroperoxide that is produced in the reaction, namely, cumene hydroperoxide, however, any suitable hydrocarbon hydroperoxide can be used including both aromatic and paraffinic hydroperoxides. Suitable hydroperoxide initiators include ethylbenzene hydroperoxide, isobutane hydroperoxide, isopentane hydroperoxide, and the like.

This barium oxide provides a significant catalytic effect during the oxidation reaction by substantially increasing the rate of the desired oxidation reaction at high selectivity. The oxidation reaction can be stopped when the solution contains from about 10 to about 30 percent cumene hydroperoxide. The concentration of cumene hydroperoxide in this solution can be increased by distilling off sufficient cumene to form a solution containing between about 50 to 90 percent cumene hydroperoxide.

DESCRIPTION OF PREFERRED EMBODIMENTS

In the following examples the cumene contained no reactive impurities and a maximum of 1.0 weight percent inert hydrocarbon isomers. The barium oxide, BaO, was 97.5 percent pure with barium carbonate and strontium oxide comprising the major impurities and was used as a 60–80 mesh powder. The air was dried to remove water and treated to remove carbon dioxide. A 300 milliliter glass reactor with stirrer and heating jacket was used for these experiments.

EXAMPLE 1

Cumene hydroperoxide was prepared in separate experiments by heating 100 ml. of cumene to 110° C. in the reactor without barium oxide present and then with barium oxide present. In the first experiment one ml. of cumene hydroperoxide was added as an initiator. In the second experiment 0.2 g. of barium oxide was also added. Air was then bubbled through the reaction liquid at a rate of 100 cc. per minute at atmospheric pressure. The concentration of cumene hydroperoxide was determined by standard iodometric titration. After three hours the concentration of cumene hydroperoxide in the experiment without barium oxide was 9.2 percent while the concentration of cumene hydroperoxide in the experiment using barium oxide was 29.8 percent.

EXAMPLE 2

The oxidation of cumene to produce cumene hydroperoxide was studied using various amounts of barium oxide. In such experiment 150 cc. of cumene, 5 cc. of cumene hydroperoxide initiator (80 percent cumene hydroperoxide) and a desired amount of finely divided barium oxide were charged to the reactor. Air was then bubbled through at the rate of 100 cc. per minute and a pressure of 20 psi. (137.9 kPa). The stirrer was started and the reactor was heated to 100° C. The reaction liquid was periodically analyzed by a high performance liquid chromatograph at room temperature. Since the liquid chromatograph did not decompose the cumene hydroperoxide, it gave a direct analysis of the by-products. The by-products comprised predominantly alpha,- alpha-dimethylbenzyl alcohol with minor amounts of acetophenone and alpha-methylstyrene. The results of the analyses including the by-products (B-P) and the selectivity to cumene hydroperoxide which was calculated from this data at similar yields of cumene hydroperoxide (CHP) are set forth in Table I.

Table I

| BaO, % | Time, hrs. | CHP, % | B-P, % | Select., % |
|---|---|---|---|---|
| 0 | 24 | 38.18 | 2.54 | 93.8 |
| 0.02 | 18 | 36.57 | 2.51 | 93.6 |
| 0.04 | 16 | 32.15 | 1.47 | 95.6 |
| 0.08 | 12 | 36.83 | 2.99 | 92.5 |
| 0.12 | 16 | 35.49 | 3.09 | 92.0 |
| 0.20 | 16 | 31.55 | 4.01 | 88.7 |

The rate of cumene hydroperoxide formation was also calculated for most of these experiments from the periods analyses of cumene hydroperoxide concentrations using the multiple variable regression mode to compute the reaction rates. In Tables II and III representative values for the mol percent of cumene hydroperoxide in the oxidation product and the reaction rate of cumene hydroperoxide formation in mols of cumene hydroperoxide per 100 mols of cumene feed per hour are tabulated.

Table II

| | 0% BaO | | 0.04% BaO | |
|---|---|---|---|---|
| Time, hrs. | CHP, mol % | CHP, rate | CHP, mol % | CHP, rate |
| 2 | 4.97 | 1.086 | 5.46 | 1.511 |
| 6 | 8.57 | 1.148 | 9.40 | 1.658 |
| 10 | 14.08 | 1.211 | 18.21 | 1.804 |
| 14 | 18.57 | 1.273 | 25.75 | 1.950 |
| 18 | 24.00 | 1.336 | 32.92 | 2.097 |
| 22 | 29.27 | 1.398 | — | — |
| 24 | 32.51 | 1.429 | — | — |

TABLE III

| | 0.08% BaO | | 0.12% BaO | |
|---|---|---|---|---|
| Time, hrs. | CHP, mol % | CHP, rate | CHP, mol % | CHP, rate |
| 2 | 8.9 | 2.464 | 7.31 | 1.572 |
| 6 | 18.92 | 2.453 | 12.99 | 1.632 |
| 10 | 28.84 | 2.443 | 20.18 | 1.692 |
| 14 | 37.71 | 2.433 | 26.57 | 1.753 |
| 16 | 43.90 | 2.428 | 31.68 | 1.783 |
| 18 | — | — | 33.48 | 1.813 |

The data in Tables II and III shows that the rate of cumene hydroperoxide formation peaks at a barium oxide concentration between 0.04 and 0.12 percent.

Even through the oxidation of cumene to cumene hydroperoxide in the presence of barium oxide is carried out under substantially anhydrous conditions preferably including the use of dried air and predried cumene, it is recognized that very low concentrations of water will result together with the small amount of by-products. It is believed that most of this water of reaction leaves the system but some of this water of reaction may react with the barium oxide to form a minor amount of barium hydroxide. Since barium hydroxide is an inferior catalyst for the oxidation of cumene to cumene hydroperoxide, the pressure of water results in a reduced reaction rate and a lower selectivity. Advantageously, the present procedure of using a minute amount of barium oxide results in less by-product water and therefore less of the inferior barium hydroxide in the reactor. As used herein, the expression "substantially anhydrous barium oxide" contemplates barium hydroxide as a possible minor component, while "substantially anhydrous conditions" refers to the substantial absence of free water.

It is to be understood that the above disclosure is by way of specific example and that numerous modifications and variations are available to those of ordinary skill in the art without departing from the true spirit and scope of the invention.

We claim:

1. A process for oxidizing cumene to cumene hydroperoxide comprising heating cumene in contact with about 0.0005 to about 0.15 weight percent barium oxide at a temperature between about 90° C. and about 130° C. under substantially anhydrous conditions, contacting said cumene with molecular oxygen whereby said cumene is oxidized to cumene hydroperoxide, and continuing the oxidation reaction until the concentration of cumene hydroperoxide is at least about ten weight percent.

2. A process for oxidizing cumene to cumene hydroperoxide in accordance with claim 1 in which the oxidation reaction is carried out in the presence of between about 0.001 percent and about 0.12 weight percent barium oxide.

3. A process for oxidizing cumene to cumene hydroperoxide in accordance with claim 1 in which the oxidation reaction is carried out in the presence of between about 0.002 percent and about 0.1 weight percent barium oxide.

4. A process for oxidizing cumene to cumene hydroperoxide in accordance with claim 1 in which the partial pressure of oxygen is between about 5 and about 200 psia.

5. A process for oxidizing cumene to cumene hydroperoxide in accordance with claim 1 in which the cumene is contacted with air.

6. A process for oxidizing cumene to cumene hydroperoxide in accordance with claim 1 in which a minor amount of a hydrocarbon hydroperoxide initiator is present in the reaction mixture.

7. A process for oxidizing cumene to cumene hydroperoxide in accordance with claim 6 in which the initiator is cumene hydroperoxide.

8. A process for oxidizing cumene to cumene hydroperoxide in accordance with claim 1 in which the temperature is between about 95° C. and about 120° C.

9. A process for oxidizing cumene to cumene hydroperoxide in accordance with claim 1 in which the barium oxide is in a particle size of about 20 microns to about 5 millimeters in diameter and said mixture of cumene and barium oxide is agitated.

10. A process for oxidizing cumene to cumene hydroperoxide in accordance with claim 9 in which the barium oxide is in a particle size of about 50 to about 1,000 microns.

* * * * *